(12) United States Patent
Kuzma

(10) Patent No.: US 7,949,395 B2
(45) Date of Patent: May 24, 2011

(54) IMPLANTABLE MICRODEVICE WITH EXTENDED LEAD AND REMOTE ELECTRODE

(75) Inventor: Janusz A Kuzma, Parker, CO (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 455 days.

(21) Appl. No.: 10/353,101

(22) Filed: Jan. 27, 2003

(65) Prior Publication Data

US 2003/0114905 A1 Jun. 19, 2003

Related U.S. Application Data

(62) Division of application No. 10/188,465, filed on Jul. 2, 2002, now abandoned, which is a division of application No. 09/624,130, filed on Jul. 24, 2000, now abandoned.

(60) Provisional application No. 60/156,980, filed on Oct. 1, 1999.

(51) Int. Cl.
*A61N 1/05* (2006.01)

(52) U.S. Cl. ........................................................ 607/36

(58) Field of Classification Search .................. 600/372, 600/377; 607/61, 115, 116, 36, 48
See application file for complete search history.

(56) References Cited

U.S. PATENT DOCUMENTS

| | | | |
|---|---|---|---|
| 3,522,811 A * | 8/1970 | Wingrove et al. ................ 607/27 |
| 3,718,142 A | 2/1973 | Mulier | |
| 4,143,661 A | 3/1979 | LaForge et al. | |
| RE30,366 E * | 8/1980 | Rasor et al. ..................... 607/36 |
| 4,333,469 A | 6/1982 | Jeffcoat et al. | |
| 4,379,462 A | 4/1983 | Borkan et al. | |
| 4,414,979 A * | 11/1983 | Hirshorn et al. ................ 607/51 |
| 4,432,377 A | 2/1984 | Dickhudt | |
| 4,524,774 A | 6/1985 | Hildebrandt | |
| 4,573,481 A * | 3/1986 | Bullara ......................... 607/118 |
| 4,612,934 A | 9/1986 | Borkan | |
| 4,793,353 A | 12/1988 | Borkan | |
| 4,905,285 A | 2/1990 | Allen et al. | |
| 4,989,617 A | 2/1991 | Memberg et al. | |
| 5,002,053 A * | 3/1991 | Garcia-Rill et al. ............ 607/49 |
| 5,105,811 A * | 4/1992 | Kuzma ............................ 607/57 |
| 5,179,962 A * | 1/1993 | Dutcher et al. ............... 607/128 |
| 5,193,539 A | 3/1993 | Schulman et al. | |
| 5,193,540 A | 3/1993 | Schulman et al. | |
| 5,211,175 A * | 5/1993 | Gleason et al. ............... 600/548 |
| 5,257,634 A * | 11/1993 | Kroll ............................. 607/122 |
| 5,282,468 A | 2/1994 | Klepinski | |
| 5,282,845 A * | 2/1994 | Bush et al. .................... 607/128 |
| 5,312,439 A | 5/1994 | Loeb | |
| 5,324,316 A | 6/1994 | Schulman et al. | |

(Continued)

FOREIGN PATENT DOCUMENTS

WO    WO-98/37926 A1    9/1998

(Continued)

*Primary Examiner* — Michael Kahelin
(74) *Attorney, Agent, or Firm* — Vista IP Law Group LLP

(57) ABSTRACT

An implantable microdevice includes at least one electrode detachably connected to electronic circuitry housed in an hermetically-sealed micro housing. The micro housing has a length no more than about 10 mm. In one embodiment, the electrode is located at a distal end of an electrode lead, and a proximal end of the electrode lead is removably inserted into a connector that forms part of the micro housing.

16 Claims, 4 Drawing Sheets

U.S. PATENT DOCUMENTS

| | | | |
|---|---|---|---|
| 5,358,514 A | 10/1994 | Schulman et al. | |
| 5,366,493 A * | 11/1994 | Scheiner et al. | 607/116 |
| 5,405,367 A | 4/1995 | Schulman et al. | |
| 5,458,629 A | 10/1995 | Baudino et al. | |
| 5,531,787 A | 7/1996 | Lesinski et al. | |
| 5,591,217 A * | 1/1997 | Barreras | 607/61 |
| 5,741,316 A | 4/1998 | Chen et al. | |
| 5,807,397 A | 9/1998 | Barreras | |
| 5,945,762 A | 8/1999 | Chen et al. | |
| 5,957,958 A | 9/1999 | Schulman et al. | |
| 5,991,664 A | 11/1999 | Seligman | |
| 6,051,017 A | 4/2000 | Loeb et al. | |
| 6,064,913 A | 5/2000 | Irlicht et al. | |
| 6,067,474 A | 5/2000 | Schulman et al. | |
| 6,078,838 A | 6/2000 | Rubinstein | |
| 6,092,531 A | 7/2000 | Chen et al. | |
| 6,154,677 A | 11/2000 | Leysieffer | |
| 6,154,678 A | 11/2000 | Lauro | |
| 6,185,452 B1 | 2/2001 | Schulman et al. | |
| 6,198,971 B1 | 3/2001 | Leysieffer | |
| 6,216,045 B1 | 4/2001 | Black et al. | |
| 6,219,580 B1 | 4/2001 | Faltys et al. | |
| 6,246,911 B1 | 6/2001 | Seligman | |
| 6,272,382 B1 | 8/2001 | Faltys et al. | |
| 6,289,247 B1 | 9/2001 | Faltys et al. | |
| 6,358,281 B1 | 3/2002 | Berrang et al. | |
| 6,464,687 B1 | 10/2002 | Ishikawa et al. | |
| 6,542,777 B1 | 4/2003 | Griffith et al. | |
| 6,609,032 B1 | 8/2003 | Woods | |
| 6,700,982 B1 | 3/2004 | Geurts et al. | |
| 2003/0004546 A1 | 1/2003 | Casey | |
| 2003/0114905 A1 | 6/2003 | Kuzma | |
| 2004/0059392 A1 | 3/2004 | Parramon et al. | |
| 2005/0004619 A1 | 1/2005 | Wahlstrand et al. | |
| 2006/0161204 A1 | 7/2006 | Colvin et al. | |
| 2006/0184204 A1 | 8/2006 | He | |

FOREIGN PATENT DOCUMENTS

| | | |
|---|---|---|
| WO | WO 98/43700 | 10/1998 |
| WO | WO 98/43701 | 10/1998 |

* cited by examiner

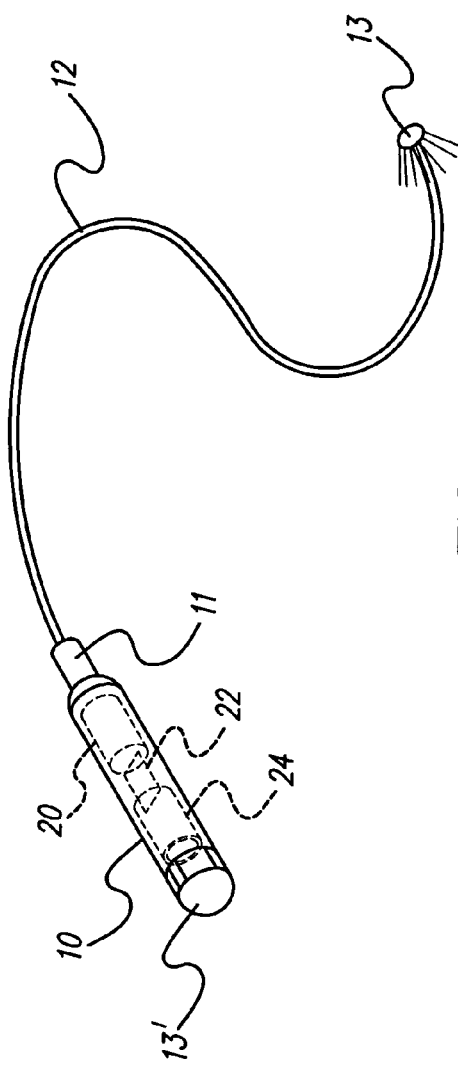
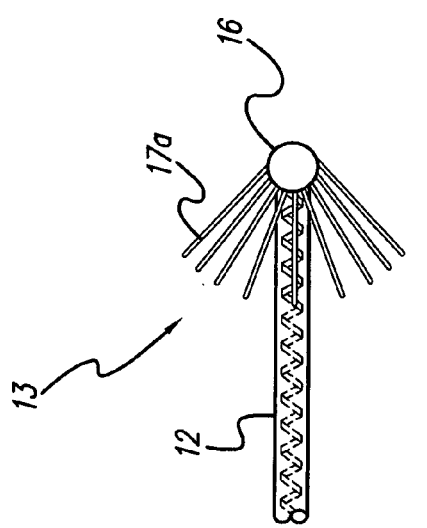
FIG. 1
FIG. 1A
FIG. 1B

IMPLANTABLE MICRODEVICE WITH EXTENDED LEAD AND REMOTE ELECTRODE

This application is a Divisional of U.S. patent application Ser. No. 10/188,465, filed Jul. 2, 2002 now abandoned, which application is a Divisional of U.S. patent application Ser. No. 09/624,130, filed Jul. 24, 2000, now abandoned, which application in turn claims the benefit of U.S. Provisional Patent Application Ser. No. 60/156,980, filed Oct. 1, 1999, which applications are all incorporated herein by reference in their entirety.

BACKGROUND OF THE INVENTION

The present invention relates to implantable medical devices, and more particularly to an implantable microminiature stimulator (or "microstimulator") or microminiature sensor (or "microsensor") comprising a microdevice and one or more remote electrodes adapted to attach to one or more muscle or nerve fibers (or muscles or nerves) and to electrically stimulate the muscle or nerve at the point of attachment in a controlled manner, or to sense one or more specific parameters that originate at or near the point of attachment. More particularly, the invention relates to an implantable microstimulator and/or microsensor (hereafter referred to as a "microdevice" or "microdevices") having a lead connecting one or more remote electrodes to the microdevice for stimulating or sensing.

Neurological disorders are often caused by neural impulses failing to reach their natural destination in otherwise functional body systems. Local nerves and muscles may function, but, for various reasons, injury, stroke, or other cause, the stimulating nerve signals do not reach their natural destination. For example, paraplegics and quadriplegics have intact nerves and muscles and only lack the brain-to-nerve link, which stimulates the muscles into action.

Prosthetic devices have been used for some time to provide electrical stimulation to excite muscles, nerves or other tissues. Such devices vary in size and complexity. For example, some systems comprise large, bulky systems feeding electrical pulses by conductors passing through the skin. However, complications, including the possibility of infection, arise in the use of muscle, nerve or other stimulators which have conductors extending through the skin or which have nerve-stimulating electrodes that puncture or penetrate the epineurium.

Small, implanted stimulators are also known in the art which are controlled through telemetry signals, such as are discussed in U.S. Pat. No. 4,524,774 (invented by Hildebrandt). However, in the use of implanted stimulators, difficulties arise in providing suitable, operable stimulators which are small in size and have the capability to receive and store sufficient energy and control information to satisfactorily operate them without direct connection. Hence, what is needed is an implantable stimulator that avoids the use of through-the-skin conductors, epineurium-penetrating electrodes, or other tissue-penetrating electrodes, and is small enough to facilitate easy implantation, yet has sufficient capacity to receive and store energy and control information so as to provide useful muscle or nerve stimulation.

The microdevices described in U.S. Pat. Nos. 5,193,539 and 5,358,514 comprise miniature devices that both receive power and control signals inductively from sources outside the body and provide stimulation or sense signals to muscles and nerves touching the device. Unfortunately, the muscle or nerve that requires stimulation or sensing is often deep inside the body and very inefficient inductive power transmission results. One solution would be to provide a battery in the microdevice. However this approach is technically difficult and would create a requirement for extensive surgery if it is necessary to remove the system in case of failure or at the end of the battery life. What is needed, therefore, is a way to efficiently power the microdevice and to provide stimulation or sensing in the desired location deep within the body.

Additionally, the microdevices described in U.S. Pat. Nos. 5,193,539 and 5,358,514 require a transmitting coil to be located outside the skin adjacent to the microdevice. In some body locations where an extreme degree of flexing takes place (for example the ankle, knee, or elbow), it would be difficult to easily attach the external coil. What is needed, therefore, is a way to power the microdevice when the electrode must be located in one of these locations.

The present invention advantageously addresses the above and other needs.

SUMMARY OF THE INVENTION

The present invention provides a microdevice, similar to existing microdevices, fitted with a connector which allows one or more leads and electrodes to be detachably connected to the microdevice, with the electrode being implanted at a stimulation and/or sensing site that may be embedded much deeper in the body tissue than would otherwise be possible using an existing microdevice.

In accordance with one aspect of the invention, a source of electrical energy located outside the skin, modulated by desired control information, is used to selectively control and drive numerous, small stimulators, each attached to (or otherwise electrically coupled to) a particular nerve, muscle, or muscle or nerve fiber located within a specific location within a patient's body. Thus, for example, a desired, progressive muscular stimulation may be achieved through the successive or simultaneous stimulation of numerous stimulators, directed by a single source of information and energy outside the body.

In accordance with another aspect of the invention, an implantable microdevice, e.g., a microstimulator or microsensor, is housed within a small, sealed, housing. When connected to an electrode, such housing includes all the requisite electronic circuitry for sensing a specified parameter, or generating electrical stimulation pulses that can be applied to a selected nerve or muscle, as well as circuitry for electromagnetically (i.e., inductively, optically, or through a radio frequency link) receiving power and control signals from an external source. The electrodes are remote from the housing and connected by a lead. Typically, the electrodes are configured for self attachment to a desired muscle or nerve, thereby permitting the microdevice to stimulate the muscle or nerve, and/or to sense a given parameter at or near the muscle or nerve. Any type of electrode attachment scheme known in the art, or yet to be developed, may be used to attach the electrode to the muscle or nerve, such as using helical, deep brain, chip, or cuff electrodes. The use of an electrode with exposed wire strands folding back on an electrode lead is preferred because such an electrode has good anchoring characteristics. Advantageously, the electrodes are sufficiently small to allow attachment to a single muscle or nerve, thereby preventing tethering of the muscle or nerve.

In accordance with yet another aspect of the invention, the microdevice includes telemetry circuitry so as to provide telemetry functions as well as stimulating and/or sensing functions. Such telemetry function allows limited information, e.g., a signal sensed by the sensing function, to be telemetered to an external location. Such telemetered information may be used as diagnostic information, e.g., to signal whether a lead or electrode has broken, or as control information, e.g., to signal whether the amplitude of a stimulating pulse needs to be adjusted. In the case of telemetering control information, a feedback system can thus be established that includes the implanted microdevice and an external controller in order to control the operation of the implanted microdevice in a desired manner.

In accordance with an additional aspect of the invention, the microdevice and remote electrode combination is of a size and weight that allows its implantation through a very small incision in the patient's skin. In some embodiments, such incision may be as small as the puncture hole of a hypodermic needle, with the microdevice being implanted through the lumen of such needle. In other embodiments, the incision may be made in conventional manner, but is still of very small dimensions, e.g., having linear dimensions of no more than about 5 to 10 mm.

In accordance with an additional aspect of the invention, the electrode lead is removably, attached to the microdevice so that in the event of replacement of the microdevice, minor surgery will allow its removal and reconnection of a new microdevice with the existing electrode lead and electrode.

It is a feature of the invention to provide multiple electrodes attached to a single electrode lead to permit sensing or stimulation of multiple muscles or nerves.

BRIEF DESCRIPTION OF THE DRAWINGS

The above and other aspects, features and advantages of the present invention will be more apparent from the following more particular description thereof, presented in conjunction with the following drawings wherein:

FIG. 1 depicts the invention comprising the microdevice, connector, electrode lead, and electrode;

FIG. 1A shows an electrode with a first electrode anchor with barbs circling the electrode lead;

FIG. 1B show an electrode with a second electrode anchor comprising bunched strands bent back over the electrode lead in a group;

Corresponding reference characters indicate corresponding components throughout the several views of the drawings.

DETAILED DESCRIPTION OF THE INVENTION

Figure 2:
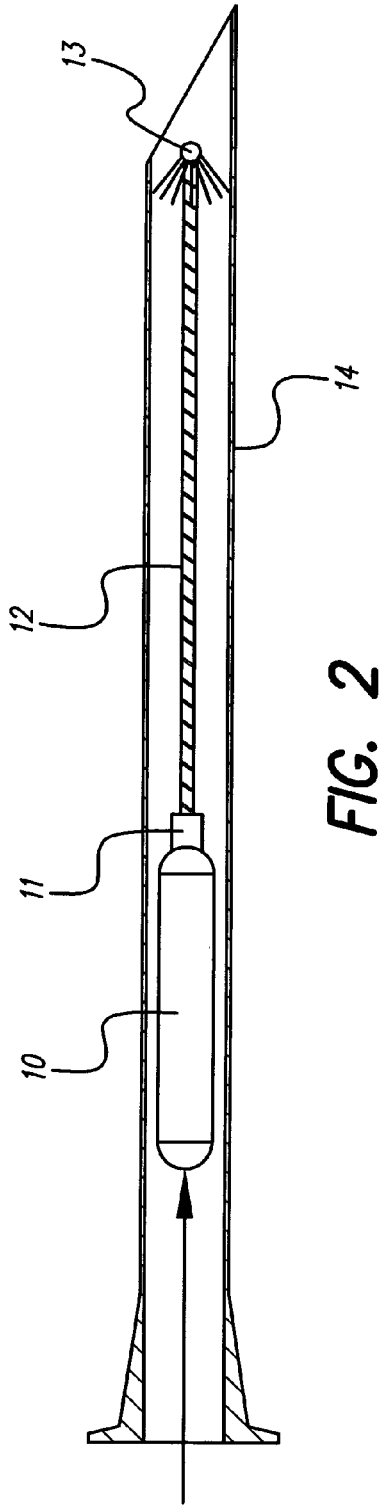
FIG. 2 depicts one method of placement using a large hypodermic needle.

The following description is of the best mode presently contemplated for carrying out the invention. This description is not to be taken in a limiting sense, but is made merely for the purpose of describing the general principles of the invention. The scope of the invention should be determined with reference to the claims.

As seen in FIG. 1, the present invention relates to a microdevice 10 that uses an electrode 13 connected at a distal end of a flexible electrode lead 12. A proximal end of the flexible electrode lead 12 is removably connected to a connector 11 on a microdevice 10 and thereby electrically connected to an electronic circuit within the microdevice 10. The electrode 13 may be located in a desired implant location, e.g., deep within body tissue near or at a desired nerve bundle or muscle tissue. The microdevice 10 may be located near the surface of the skin to facilitate electromagnetic power transmission and control. In one embodiment, the microdevice 10 comprises an electronic stimulating device that derives operating power from an externally applied alternating magnetic field; with the microdevice 10 being controlled by control information that modulates such magnetic field. In another embodiment, the microdevice 10 comprises an implantable microsensor that senses a desired biomedical parameter, e.g., voltage, body position, pressure, magnetic field, chemical parameters such as pH, oxygen, salinity, glucose concentration, or the like, converts such sensed parameter to an electrical signal (if not already an electrical signal), and telemeters such sensed signal to a location outside the body. In still another embodiment, the microdevice 10 comprises a device that provides both stimulating and sensing functions.

The design and operation of a suitable microdevice for use with the invention is described in U.S. Pat. No. 5,193,539. The microdevice circuitry is hermetically sealed in a tiny tubular housing, which housing is no more than about 10 mm in length in one embodiment described in U.S. Pat. No. 5,193, 540. The teachings of the '539 and '540 patents, while directed to a microstimulator, are also applicable to a microsensor. Means of attaching electrodes to either nerves or muscles are taught in U.S. Pat. No. 5,358,514. The '539, '540 and '514 patents are all incorporated herein by reference.

The present invention is directed to an improvement to the microdevice described in the '539, '540 and '514 patents. The '539, '540 and '514 patents describe a microdevice that either senses or stimulates nerves or muscles. The microdevice described in the '514 patents uses electrodes exposed to the tissue surrounding the microdevice to stimulate nerves or muscles, or to sense signals in nerves or muscles. An electronic circuit within a microstimulator processes control signals to determine the commanded stimulation, and generates the stimulation signal for the electrode. In another embodiment, a microsensor includes an electronic circuit which processes the control signals to determine how signals received by the electrode will be processed, and processes sensed biomedical signals. In yet another embodiment the microdevice both stimulates tissue and senses. In such embodiment the electrical circuit processes control signals for both stimulation and sensing, and the electrical circuit provides the stimulation signal to the electrode and processes sensed biomedical signals.

The microdevice receives both power and control signals inductively from a primary (non-implanted) transmitting coil removably attached to or near the skin. The power received inductively by a microdevice may be stored in a capacitor contained in the microdevice. This means of providing both power and control has the significant advantage of not requiring that any wiring extend through the skin, thus reducing the occurrence of infection. However, the efficiency of inductive energy transfer declines rapidly if the secondary coil 20, i.e., the coil within the microdevice, is moved away from the primary coil. In applications where the nerve or muscle to be sensed or stimulated is deep within the body, this separation reduces the energy transfer to an unacceptable level. Additionally, if the nerves or muscles are in a location where substantial flexing of the body takes place (i.e. knee, ankle, elbow), it may be impossible to position the external primary coil adjacent to the microdevice 10 even when the microdevice 10 is not deep within the body. One of the envisioned applications of the microdevice 10 is the relief of chronic pain, and these joints (knee, ankle, elbow), are common sources of pain due to injury or aging. One solution to the energy transfer problem would be to increase the size of the external primary coil, but one of the principle advantages of the microdevice 10 is its small size. The requirement for a bulky external primary coil would substantially diminish this advantage. Another solution is to place a battery 24 in the microdevice to provide power, such as is disclosed in International Patent Application PCT/US98/03687, filed Feb. 25, 1998, and published as document WO 98/37926 on Sep. 3, 1998, which publication is incorporated herein by reference.

The present invention solves the energy transfer problem by utilizing one or more remote electrodes 13 connected to the microdevice 10 by an electrode lead 12 and connector 11. For stimulation and sensing to occur, a pair of electrodes is required, a primary electrode (usually referred to as simply the "electrode") and a return electrode. A return electrode 13' is typically formed on the case of the microdevice 10. If a more focused stimulation is desired, both the electrode 13 and return electrode 13' may be located at a distal end of the lead 12.

The electrode 13 comprises an electrode head 16 and a first electrode anchor 17a, as seen in FIG. 1A. In FIG. 1A, the first electrode anchor 17a comprises a family of barbs circling the electrode head 16 and pointing or extending back along the electrode lead 12. When the invention is inserted using a hypodermic needle 14, as explained below in connection with FIGS. 2, 2A, and 2B, the first electrode anchor 17a tends to fix the location of the electrode 13 as the hypodermic needle 14 is removed.

The electrode anchor may reflect several embodiments and is not functionally limited to the embodiment shown in FIG. 1A. In FIG. 1B, for example, a second electrode anchor 17b, which is a preferred embodiment, is shown. The second electrode anchor 17b comprises several loose non-insulated wire strands that extend from the end of the electrode lead 12 and fold 150-180 degrees back along the body of the electrode lead 12. Unlike the first electrode anchor 17a which encircles the electrode head 16, the wires of second electrode anchor 17b are bunched together and fold back over the end of the electrode lead as a group.

The microdevice 10, connector 11, electrode lead 12 and electrode 13 combination is sufficiently small to allow insertion using a hypodermic needle 14, as shown in FIG. 2. The combination may be loaded into the hypodermic needle 14, as shown in FIG. 2, and implanted by withdrawing the needle as the plunger is depressed, thus leaving the combination of the electrode 13 and microdevice 10 in the desired tissue location.

Alternatively, the electrode lead 12 and electrode 13 may be implanted using conventional tunneling and surgical techniques, and the microdevice may be implanted through a small incision, with the electrode lead 12 being connected to the microdevice 10 by way of the connector 11.

Figure 2A:
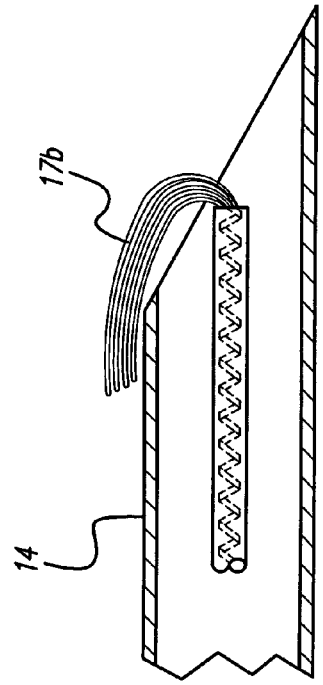
FIG. 2A shows the invention in a hypodermic needle with the first electrode anchor.
Figure 2B:
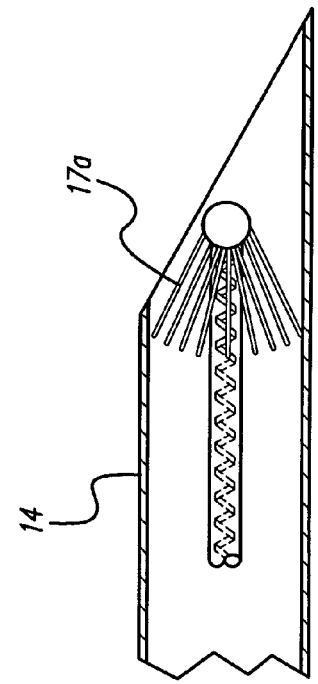
FIG. 2B shows the invention in a hypodermic needle with the second electrode anchor.

The first electrode anchor 17a is shown loaded in the hypodermic needle 14 in FIG. 2A, and the second electrode anchor 17b is shown loaded in the hypodermic needle 14 in FIG. 2B. Folding the anchor leads 17b back over the outside edge of the hypodermic needle 14, as shown in FIG. 2B, is particularly advantageous because as the sharp point of the needle penetrates the target tissue, the anchor leads 17b slide through the surrounding tissue. Then, as the needle is slowly withdrawn from the target tissue, the anchor leads 17b engage the target tissue and remain embedded therein.

An additional feature of the invention is that the microdevice 10 is removably, connected to the electrode lead 12 by the connector 11. The majority of the complexity of the invention, including the electronic circuitry, is in the microdevice 10. As a result, should a failure occur, such failure would most likely be the result of a failure within the microdevice 10. In the event of such a failure, the microdevice 10 may be detached from the electrode lead 12 and replaced with a new microdevice, which may be reconnected to the electrode lead 12, using only minor surgery because the microdevice 10 is not implanted deep within the body.

It should be noted that use of the present invention may result in a tethering effect (i.e. tying the nerves or muscles together) that has the potential to cause pain or irritation. However, by making the electrode lead 12 from materials that are super-flexible, and by using, an insertion technique that results in slack in the electrode lead 12, any tethering effects should be eliminated or minimized.

Figure 3B:
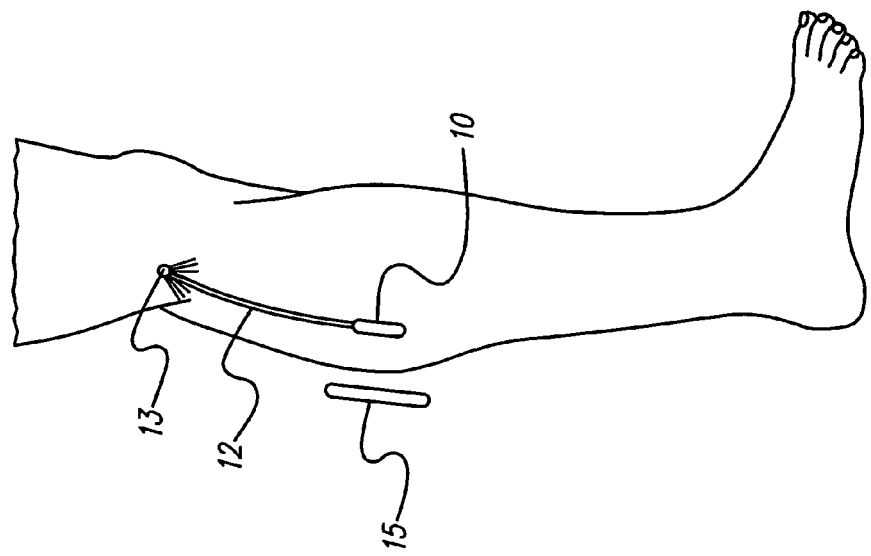
FIG. 3B illustrates location of the electrode in a tissue location that regularly bends or flexes.
Figure 3A:
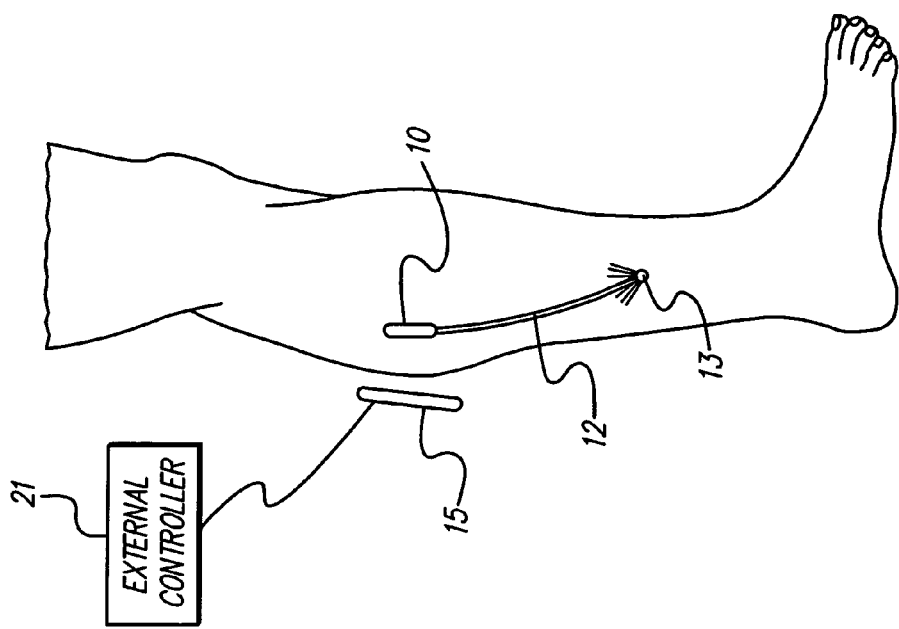
FIG. 3A depicts a typical placement of the invention.

The invention is used as illustrated, e.g., in FIG. 3A. That is, the microdevice 10 and electrode 13 are implanted into the tissue of a patient, e.g., into the leg tissue on a patient, with the electrode 13 positioned at the desired stimulation/sensing site, and with the microdevice 10 being positioned near the skin surface. The electrode lead 12 electrically connects the electrode 13 to the microdevice 10. An external primary coil 15, connected to an external controller 21, provides operating power and control signals to the microdevice 10.

As seen in FIG. 3B, the invention has particular applicability to those situations where the electrode 13 needs to be implanted in a tissue location, such as a knee joint, that flexes or bends. With the invention, the electrode 13 may be positioned at or near such flexing location, and the microdevice 10 may be implanted some distance therefrom, thereby facilitating use of the external primary coil 15 with the microdevice 10.

Figure 4:
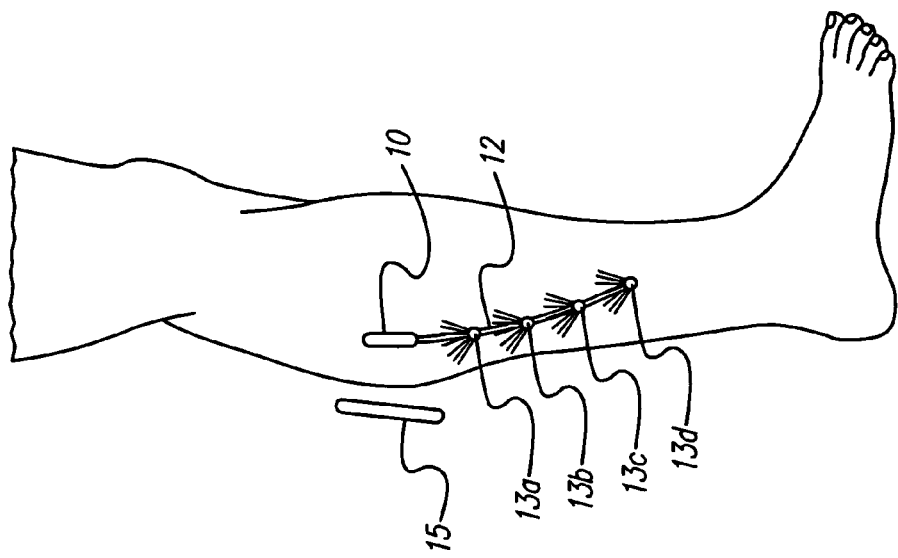
FIG. 4 depicts a multi-electrode embodiment of the invention.

In many applications of the present invention, it is desirable to stimulate or sense a group of tissue points, in close proximity to each other, to achieve an intended result. In these cases, a multi-dimensional array of microdevices 10 may be used. Advantageously, in such situations, the number of microdevices 10 required may be reduced significantly by utilizing a multi electrode embodiment of the present invention as shown in FIG. 4. A plurality of electrodes 13a, 13b, 13c, and 13d are spaced along the electrode lead 12 to achieve the desired result. The microdevice 10 and electrodes 13a, 13b, 13c, and 13d may still be inserted using a hypodermic needle 14 in much the same manner as with a single electrode 13. The hypodermic needle 14 is withdrawn at a defined rate to position the electrodes 13 in the desired positions. When the microdevice 10 and electrodes 13a, 13b, 13c, and 13d are implanted through a straight needle, the electrodes 13a, 13b, 13c, and 13d position are substantially co-linear in position. A curved needle may be employed, as required, to achieve a non co-linear electrode placement.

Figure 5:
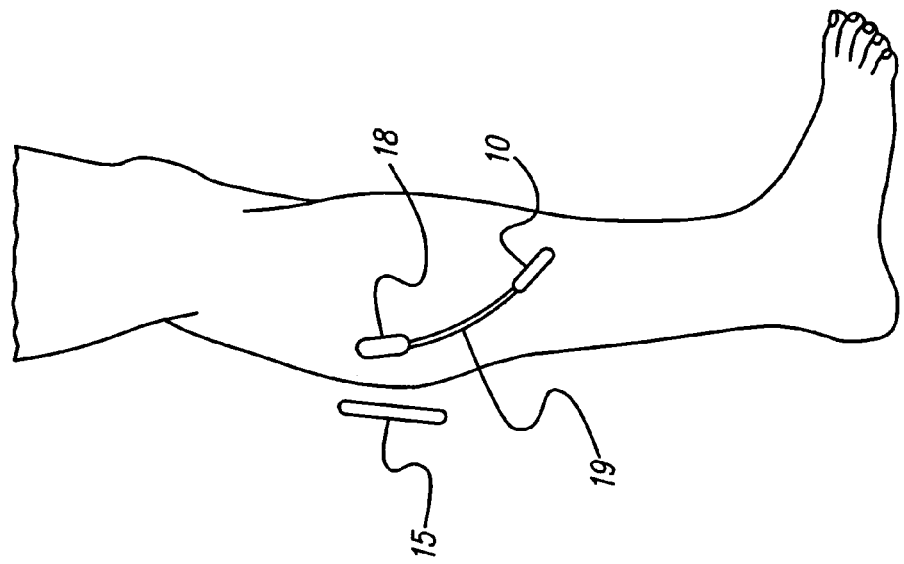
FIG. 5 illustrates an alternative embodiment of the invention wherein the microdevice is deeply implanted within body tissue and a secondary coil is positioned near the skin surface to facilitate transferring power and control signals to the microdevice from an external primary coil.

In some applications, as seen in FIG. 5, there may be a requirement to locate the microdevice 10 deep within the body. This is likely where either sensor measurements, of biological signals, are being made that may not be made remotely, or when the signal generated by the sensor is so weak that it must be processed before it can be transmitted even a short distance without being corrupted. In such case, an alternative embodiment provides an implantable secondary coil 18 remotely located from the microdevice 10, so as to place the secondary coil 18 near the primary coil 15, for efficient power transfer. The secondary coil 18 is connected to the microdevice 10 by way of a secondary coil lead 19. As in the case where the electrodes 13 are remotely located, in order to avoid tethering the nerves or muscles, the secondary coil lead 19 comprises a flexible lead. Other aspects of such embodiment are as described above for a microdevice with an electrode lead and remote electrode.

The above description generally refers to a microstimulator having an electrode for stimulating tissue or for sensing biomedical parameters. Those skilled in the art will recognize that other biomedical sensors may similarly benefit from the placement of such sensor on the distal end of a lead, and that such sensor falls within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. An implant assembly, comprising:
    a hypodermic needle; and
    an implantable device including:
        a microdevice containing electrical circuitry;
        a lead with a proximal end and a distal end, the proximal end of the lead being attached and electrically connected to the electrical circuitry of the microdevice;
        an electrode at the distal end of the lead, the electrode being electrically connected to the electrical circuitry of the microdevice via the lead; and
        anchors disposed at the distal end of the lead, wherein the anchors, when the implantable device is loaded within the hypodermic needle, are configured to fold back against an exterior of the hypodermic needle as the hypodermic needle is introduced into tissue, such that the anchors engage the tissue and affix the electrode relative to the tissue while the hypodermic needle is withdrawn from the tissue, wherein the anchors comprise non-insulated loose wire strands.

2. The implant assembly of claim 1, wherein the electrical circuitry of the microdevice comprises:
    means within the microdevice for electromagnetically receiving power from an external source; and
    means within the microdevice for electromagnetically receiving control signals from the external source.

3. The implant assembly of claim 1 further comprising additional electrodes spaced along the lead.

4. The implant assembly of claim 1 wherein the microdevice comprises at least one of a sensor and a stimulator.

5. The implant assembly of claim 1, wherein the anchors comprise a collection of anchoring members connected to the lead and bunched together on a side of the lead, wherein the anchoring members project laterally outward from the lead and proximally toward the proximal end of the lead along an extent that is in the vicinity of an outer surface of the lead.

6. The implant assembly of claim 5 further comprising additional electrodes spaced along the lead.

7. The implant assembly of claim 1, further comprising a connector disposed on the microdevice, wherein the proximal end of the lead is removably attached and electrically connected to the electrical circuitry of the microdevice via the connector.

8. The implant assembly of claim 1, wherein the anchors are configured for affixing the location of the electrode within the tissue as the hypodermic needle is withdrawn from the tissue.

9. The implant assembly of claim 1, wherein the anchors are disposed on the lead distal to the electrode.

10. The implant assembly of claim 1, wherein the anchors, when the entirety of the implantable device is loaded within the hypodermic needle, are configured to fold back against an exterior of the hypodermic needle as the hypodermic needle is introduced into tissue.

11. A method of using the implant assembly of claim 1, comprising:
    introducing the hypodermic needle into the tissue as the anchors are folded back against the exterior of the hypodermic needle; and
    withdrawing the hypodermic needle from the tissue, wherein the anchors engage and remain embedded in the tissue, such that the microdevice and electrode are left in a desired tissue location.

12. The method of claim 11, wherein the microdevice is implanted near a skin surface, and the electrode is implanted at a site remote from the microdevice.

13. The method of claim 12, wherein the electrode is implanted deep within the body of the patient.

14. The method of claim 11, wherein the implantable device further comprises a secondary coil connected to the microdevice, and wherein the microdevice is implanted deep within the body of the patient, and the secondary coil is implanted near a skin surface.

15. The method of claim 11, further comprising attaching the electrode to muscle or nerve fibers.

16. The method of claim 11, further comprising:
    disconnecting the microdevice from the lead;
    removing the microdevice from the body, while leaving the lead in the body;
    introducing another microdevice into the body; and
    connecting the other microdevice to the lead.

* * * * *